United States Patent
Ortt et al.

(10) Patent No.: US 10,408,612 B1
(45) Date of Patent: Sep. 10, 2019

(54) APPARATUS FOR NON-CONTACT OPTICAL EVALUATION OF CAMSHAFT LOBE SURFACE ROUGHNESS

(71) Applicant: TOYOTA MOTOR ENGINEERING & MANUFACTURING NORTH AMERICA, INC., Plano, TX (US)

(72) Inventors: Jonathan C. Ortt, Ripley, WV (US); Cheryl A. Rollins, Letart, WV (US); Samuel H. Bauer, Rutland, OH (US); William R. Coulter, II, Nitro, WV (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 0 days.

(21) Appl. No.: 16/020,337

(22) Filed: Jun. 27, 2018

(51) Int. Cl.
| | |
|---|---|
| *G01B 11/24* | (2006.01) |
| *G01B 11/30* | (2006.01) |
| *G01M 13/022* | (2019.01) |
| *G01N 21/88* | (2006.01) |

(52) U.S. Cl.
CPC .......... *G01B 11/30* (2013.01); *G01M 13/022* (2013.01); *G01N 21/8803* (2013.01)

(58) Field of Classification Search
CPC .......... F01L 1/047; G01B 11/00; G01B 11/24; G01B 5/0002; G01B 5/0025; G01B 5/003; G01N 21/952; G01S 17/08; G01S 17/4811; G01S 17/4817
USPC ................... 356/237.1–237.5, 600–623, 426
See application file for complete search history.

(56) References Cited

U.S. PATENT DOCUMENTS

| | | | | |
|---|---|---|---|---|
| 4,576,482 | A | | 3/1986 | Pryor |
| 4,875,776 | A | * | 10/1989 | Pryor ................. G01B 11/2433 356/625 |
| 5,114,230 | A | * | 5/1992 | Pryor ................. G01B 11/2433 209/586 |
| 5,508,944 | A | * | 4/1996 | Danielli ................. G01B 7/287 33/519 |
| 6,449,044 | B1 | * | 9/2002 | Pawa ..................... G01B 11/26 123/406.58 |
| 8,534,169 | B2 | * | 9/2013 | Miyamoto ............... B23B 5/08 700/195 |
| 9,247,213 | B2 | * | 1/2016 | Aono ................. G01N 21/9515 |
| 9,874,529 | B2 | * | 1/2018 | Morrison, III ..... G01N 21/9515 |
| 10,132,618 | B2 | * | 11/2018 | Isei ........................ G01B 11/25 |
| 10,190,860 | B2 | * | 1/2019 | Richards ............. G01B 5/0002 |
| 2002/0101595 | A1 | | 8/2002 | Johnson |

(Continued)

FOREIGN PATENT DOCUMENTS

| | | |
|---|---|---|
| EP | 1 251 330 A1 | 10/2002 |
| JP | 10-227625 A | 8/1998 |

(Continued)

*Primary Examiner* — Hoa Q Pham
(74) *Attorney, Agent, or Firm* — Oblon, McClelland, Maier & Neustadt, L.L.P.

(57) ABSTRACT

The present disclosure relates to an apparatus and method for visual inspection of a radial surface of a camshaft lobe. Upon visual inspection of the radial surface of the camshaft lobe via the apparatus and method of the present disclosure, surface roughness, or 'chatter', can be evaluated. Rapid evaluation of camshaft lobe chatter provides for improved manufacturing efficiency and decreased production delays.

20 Claims, 9 Drawing Sheets

(56) References Cited

U.S. PATENT DOCUMENTS

| | | | |
|---|---|---|---|
| 2015/0226639 A1* | 8/2015 | Cavanaugh | F01L 1/047 73/114.77 |
| 2017/0052024 A1 | 2/2017 | Reece, Jr. et al. | |
| 2017/0059298 A1 | 3/2017 | Richards et al. | |

FOREIGN PATENT DOCUMENTS

| | | |
|---|---|---|
| JP | 2003-14429 A | 1/2003 |
| JP | 2011-247242 A | 12/2011 |
| JP | 2012-181150 A | 9/2012 |

\* cited by examiner

APPARATUS FOR NON-CONTACT OPTICAL EVALUATION OF CAMSHAFT LOBE SURFACE ROUGHNESS

BACKGROUND

Field of the Disclosure

The present disclosure relates to surface roughness evaluation of camshaft lobes for automotive vehicles.

Description of the Related Art

As a part of automotive engine manufacturing, during camshaft lobe fabrication, it is not uncommon for surface finishing of the camshaft lobe to impart defects along the radial surface of the camshaft lobe. These defects, during engine operation, may lead to knocking or clicking sounds, commonly referred to as 'chatter'. While the defects that lead to 'chatter' are acceptable at certain levels, determining the magnitude of potential chatter during, for example, high volume automotive manufacturing, can be costly and may require shutting down entire manufacturing lines during component evaluation. U.S. Patent Application Publication No. 2017/0059298 A1 entitled "Camshaft sidewall measuring devices and methods thereof" by Richards and Corrado, is directed to an apparatus employing a contacting method for determining surface roughness of camshaft components, the apparatus requiring cumbersome logistical hurdles and system controls. An approach that provides for rapid, visual inspection of camshaft component surface roughness has yet to be developed.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to an apparatus for evaluating a surface roughness of a surface area of a radial surface of a camshaft lobe, comprising a light source having an emitted light ray axis, a jig having a light mount portion and a board mount portion, and a board having a board display surface and a jig mount surface, wherein a standoff distance, defined as a distance between the light mount portion and the board mount portion, is based upon a reflectivity of the surface area of the radial surface of the camshaft lobe, wherein the jig mount surface of the board is coupled to a board mount surface of the board mount portion of the jig, wherein the light source is coupled to the light mount portion of the jig.

The present disclosure further relates to a method for evaluating a surface roughness of a surface area of a radial surface of a camshaft lobe, comprising abutting a board display surface of a board against a lateral surface of the camshaft lobe, determining, via a scale bar, a first surface roughness of an initial surface area of the radial surface of the camshaft lobe, comparing the first surface roughness of the initial surface area of the radial surface of the camshaft lobe to a pre-determined threshold, and determining, via the scale bar, a second surface roughness of a subsequent surface area of the radial surface of the camshaft lobe based upon the comparison of the first surface roughness of the initial surface area of the radial surface of the camshaft lobe and the pre-determined threshold, wherein the determining of the surface roughness is based upon a reflected light array projected on the board display surface of the board, wherein the board, having the board display surface, is coupled to a board mount surface of a board mount portion of a jig via a jig mount surface, wherein the reflected light array is light emitted from a light source coupled to a light mount portion of the jig, the light source having an emitted light ray axis, wherein the light mount portion is separated from the board mount portion by a standoff distance, the standoff distance being based upon a reflectivity of the surface area of the radial surface of the camshaft lobe.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Manufacturing production delays, at times the result of quality control issues, are a constant concern and potentially costly occurrence in the automotive industry. As related to engine manufacturing and chatter-related surface finishing of camshaft lobes, in particular, quality control issues often result in extended, complete line stoppage in order to allow for thorough investigation of the issue, evaluation of the component, and determination of how significant the chatter-related issue may be. This thorough process, however, can be time intensive and result in significant, compounding production delays. A rapid and accurate visual triage process for evaluation of chatter of camshaft lobes can minimize production delays and improve production line efficiency.

Figure 1:
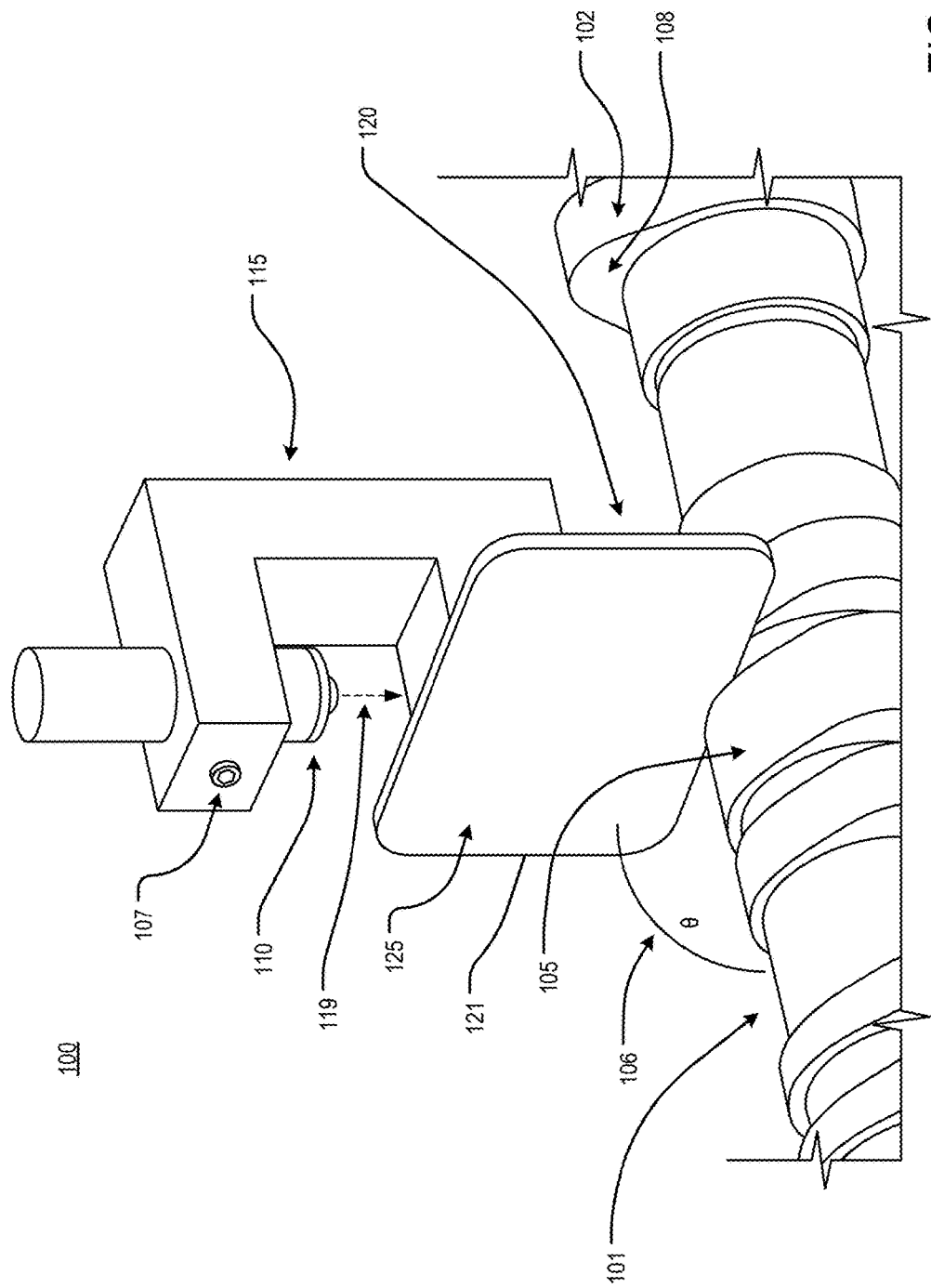
FIG. 1 is a schematic of a perspective view of a chatter evaluation tool in a testing environment, according to an embodiment of the present disclosure.

FIG. 1 is a schematic of a perspective view of a chatter evaluation tool in a testing environment, according to an exemplary embodiment of the present disclosure. The chatter evaluation tool 100 comprises a board 120 coupled to a board mount portion of a jig 115. A light source 110 is fixed within a light mount portion of the jig 115 by a set screw 107. Light rays emitted from the light source 110 are emitted substantially along an emitted light ray axis 119. In an embodiment, the light source 110 is positioned relative to a board display surface 125 such that light rays from the light source 110 are emitted along an axis parallel to a first dimension 121 of the board 120. In another embodiment, light rays from the light source 110 are emitted along an axis forming a pre-determined angle with the first dimension 121 of the board 120. In an example, the pre-determined angle formed between the first dimension 121 of the board 120 and the emitted light ray axis 119 is between −85°. and +85°. In another example, the angle formed between the first dimension 121 of the board 120 and the emitted light ray axis 119 is between −45°. and +45°. In a preferred example, the angle formed between the first dimension 121 of the board 120 and the emitted light ray axis 119 is 0°.

Further, the light source 110 is positioned relative to the board display surface 125 such that a pre-determined percentage of emitted light is reflected by a radial surface 105 of the camshaft lobe 102. In an embodiment, the light source 110 is positioned such that the pre-determined percentage of emitted light reflected by the radial surface 105 of the camshaft lobe 102 is between 1% and 100%. In an example, the light source 110 is positioned such that the pre-determined percentage of emitted light reflected by the radial surface 105 of the camshaft lobe 102 is between 25% and 75%. In a preferred example, the light source 110 is positioned such that the pre-determined percentage of emitted light reflected by the radial surface 105 of the camshaft lobe 102 is 50%.

According to an embodiment of the present disclosure, a surface of the board 120 abuts a radial surface of a camshaft 101 and is proximate to a lateral surface 108 of a camshaft lobe 102. Further, the chatter evaluation tool 100 is oriented such that the board display surface 125 of the board 120 forms a pre-determined angle 106 with a longitudinal axis of the camshaft 101. In an example, the angle 106 formed between the board display surface 125 of the board 120 and the longitudinal axis of the camshaft 101 is between 5° and 175°. In another example, the angle 106 formed between the board display surface 125 of the board 120 and the longitudinal axis of the camshaft 101 is between 45° and 135°. In a preferred example, the angle 106 formed between the board display surface 125 of the board 120 and the longitudinal axis of the camshaft 101 is 90°.

The angle formed between the first dimension 121 of the board 120 and the emitted light ray axis 119, the position of the light source 110 relative to the board display surface 125 of the board 120, and the angle formed between the board display surface 125 of the board 120 and the longitudinal axis of the camshaft 101 are determined such that a visually discernable reflected light array is projected onto the board display surface 125 of the board 120.

In another embodiment, the light source 110 is positioned relative to the longitudinal axis of the camshaft 101 such that light rays from the light source 110 are emitted along an emitted light ray axis 119 perpendicular to the longitudinal axis of the camshaft 101. In another embodiment, light rays from the light source 110 are emitted along an emitted light ray axis 119 forming a pre-determined angle with the longitudinal axis of the camshaft 101. In an example, the pre-determined angle formed between the longitudinal axis of the camshaft 101 and the emitted light ray axis 119 is between −85° and +85°. In another example, the angle formed between the longitudinal axis of the camshaft 101 and the emitted light ray axis 119 is between −45° and +45°. In a preferred example, the angle formed between the longitudinal axis of the camshaft 101 and the emitted light ray axis 119 is 0°.

Further, the above-described relationships can be adjusted in response to changes in the intensity of the light source, the reflectivity of the radial surface of the camshaft lobe, and the ambient conditions of the testing environment in order to create a reflected light array suitable for rapid visual inspection.

Figure 2:
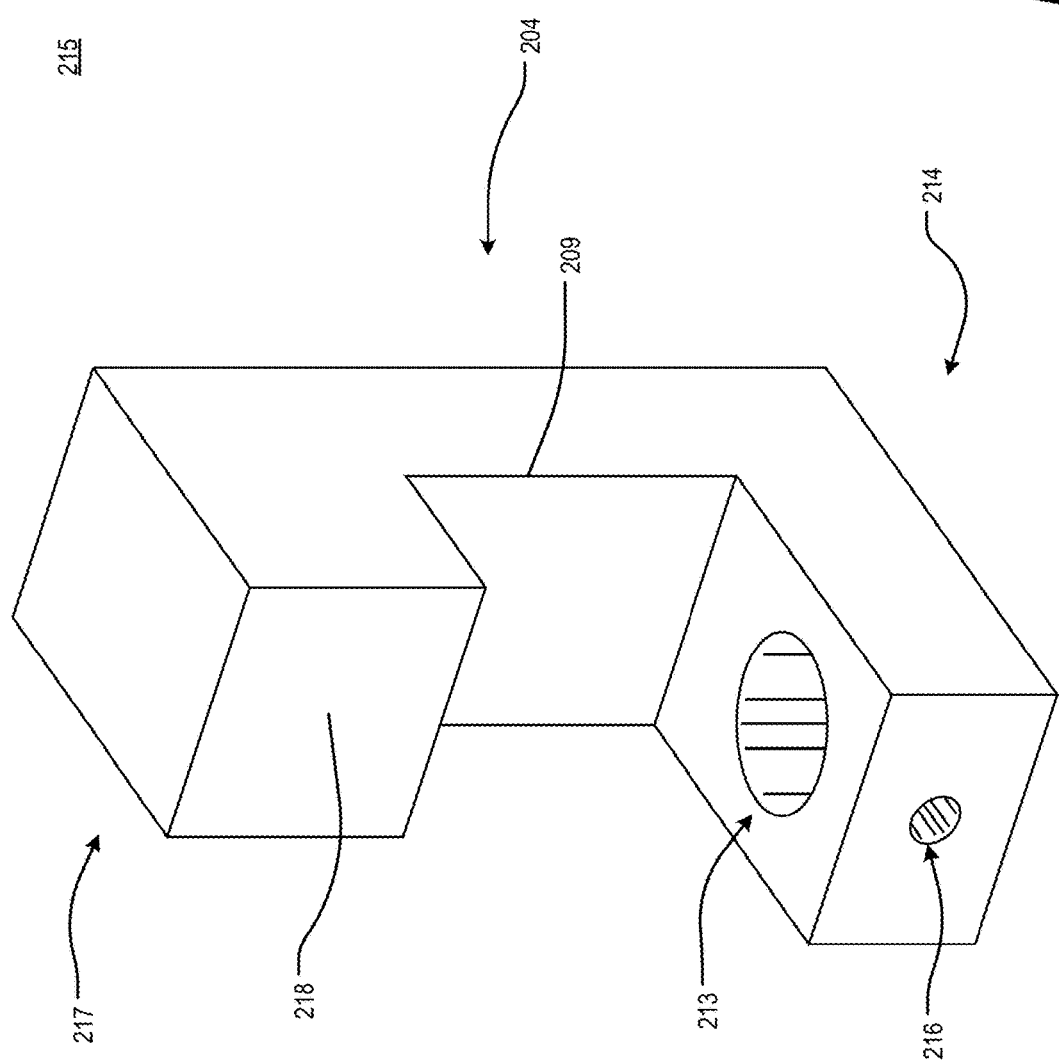
FIG. 2 is a schematic of a jig of a chatter evaluation tool, according to an embodiment of the present disclosure.

FIG. 2 is a schematic of a perspective view of the jig of the chatter evaluation tool of the present disclosure. The jig 215 is comprised of a light mount portion 214, a standoff portion 204, and a board mount portion 217. According to an embodiment, the light mount portion 214 is comprised of a light mount clearance 213. The light mount clearance 213 is configured to allow for free movement of a light source. According to an embodiment, the light mount portion 214 further comprises a tapped hole 216. The tapped hole 216 is configured to allow for mechanical coupling, via thread and screw mechanism, with a set screw. In an embodiment, the tapped hole 216 is positioned in order to allow for, upon rotation of the set screw, compression of the set screw against a surface of the light source, thus reversibly fixing the light source within the light mount clearance 213. The light source can be reversibly fixed at a height relative to the radial surface of the camshaft lobe. Alternatively, in another embodiment, the vertical position of the light source can be adjusted based upon a reflectivity of a radial surface of a camshaft lobe.

According to an embodiment of the present disclosure, the light source is fixed within the light mount clearance 213 by a set screw mechanism via tapped hole 216. It should be appreciated that the set screw mechanism described herein is merely representative of a variety of techniques for reversibly fixing a light source within a mount, as would be understood by one of ordinary skill in the art.

According to an embodiment, the light mount portion 214 is separated from the board mount portion 218 by the standoff portion 204. The standoff portion 204 comprises a standoff distance 209. The standoff distance 209 can be pre-determined according to the specifications of an individual camshaft, wherein the standoff distance 209 is pre-determined and can be modified based upon the reflectivity of the radial surface of the camshaft lobe in order to discernibly project a reflected light array onto a board display surface. In an example, the standoff distance 209 can be increased for a highly reflective surface and decreased for a minimally reflective surface. In a further embodiment, the standoff distance 209 can be modified in order to ensure 360° rotation of the camshaft is possible without obstruction by the light source or light mount portion 214 of the jig 215.

According to an embodiment, the board mount portion 217 comprises a board mount surface 218. In an embodiment, the board mount surface 218 is of sufficient dimensions for coupling with a jig mount surface of the board.

Figure 3:
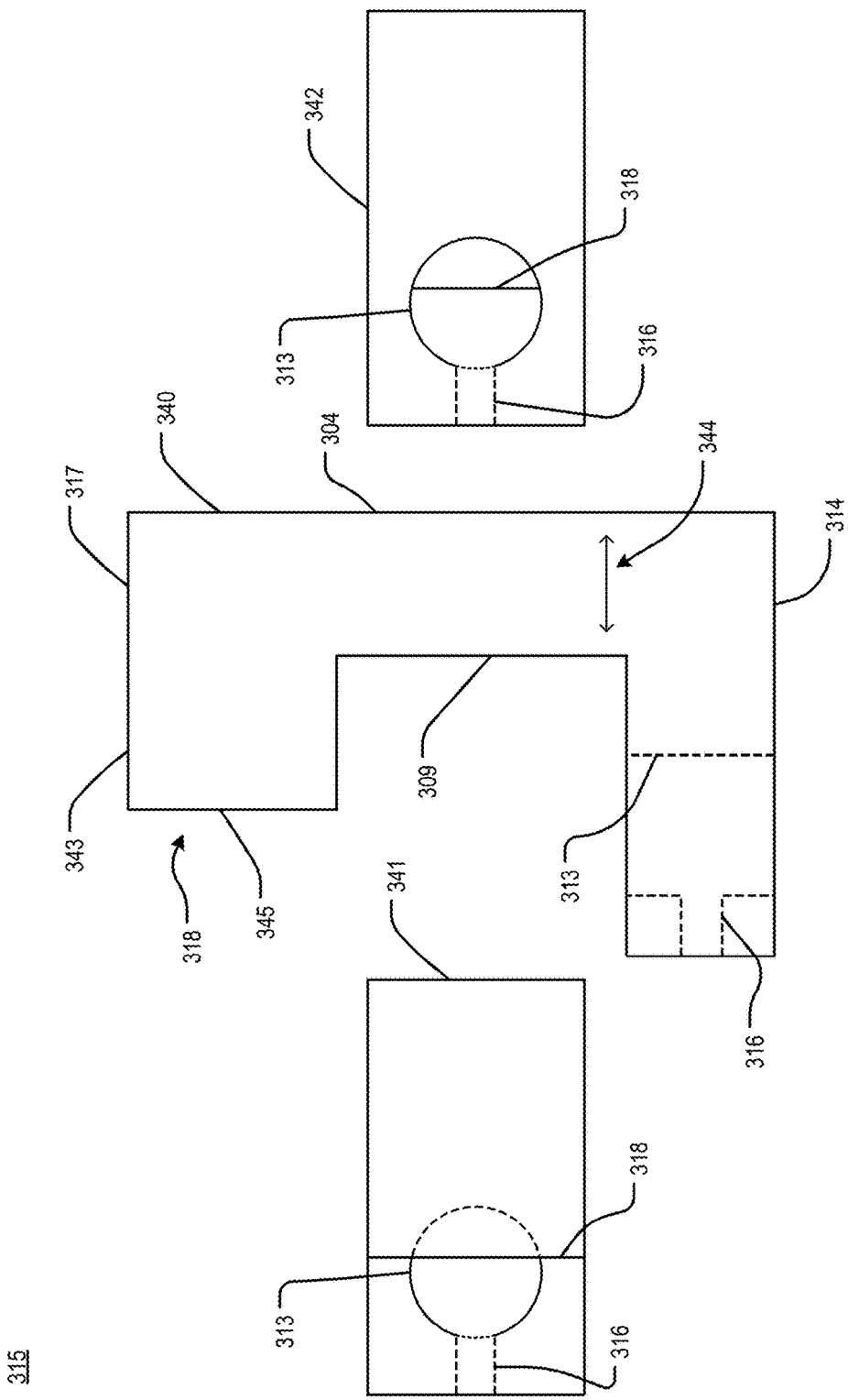
FIG. 3A is a schematic of a bottom view of a jig of a chatter evaluation tool, according to an embodiment of the present disclosure.
FIG. 3B is a schematic of a side view of a jig of a chatter evaluation tool, according to an embodiment of the present disclosure.
FIG. 3C is a schematic of a top view of a jig for a chatter evaluation tool, according to an embodiment of the present disclosure.

Exemplary dimensions of the jig of the present disclosure are described alongside the schematics of FIG. 3A, FIG. 3B, and FIG. 3C.

FIG. 3A is a schematic of a bottom view of a jig of the chatter evaluation tool. According to an exemplary embodiment of the present disclosure, a light mount portion of the jig 315 comprises a light mount clearance 313 and a tapped hole 316. The board mount portion of the jig 315 comprises a board mount surface 318. The board mount surface 318 is positioned such that the coupling of a board to the board mount surface 318 ensures light rays from a light source are emitted in a pre-determined manner. In an example, and as alluded to above, the light source is configured relative to the board such that a pre-determined percentage of light rays (e.g. 50%) are emitted onto a radial surface of a camshaft lobe.

FIG. 3B is a schematic of a lateral view of a jig of the chatter evaluation tool. According to an exemplary embodiment of the present disclosure, the light mount portion 314 of the jig 315 comprises the light mount clearance 313 and the tapped hole 316. A standoff portion 304 separates the light mount portion 314 from the board mount portion 317 by a standoff distance 309. The standoff distance 309 is pre-determined and can be modified based upon the reflectivity of the radial surface of the camshaft lobe in order to allow for discernible projection of a reflected light array onto a board display surface. In another embodiment, the standoff distance 309 is determined such that the light mount portion 314 of the jig 315 does not impede a 360° rotation of the camshaft during evaluation. The board mount portion 317 is comprised of the board mount surface 318 with dimensions appropriate for securing the board. The board may be coupled to the board mount portion 317 by a variety of methods including but not limited to adhesives, fasteners, and welding, as would be understood by one of ordinary skill in the art. In an embodiment, the position of the board mount surface 318, in a lateral view, relative to the position of the light mount clearance 313, in a lateral view, is configured such that a pre-determined percentage of emitted light rays reach the radial surface of a camshaft lobe.

FIG. 3C is a schematic of a top view of a jig of the chatter evaluation tool. According to an exemplary embodiment of the present disclosure, the light mount portion of the jig 315 comprises the light mount clearance 313 and the tapped hole 316. An aspect of the board mount surface 318 is visible through the light mount clearance 313. The position of the board mount surface 318, slightly offset from a diameter of the light mount clearance 313, is such that a light source is provided in a pre-determined position.

In an embodiment, the jig 315 can be fabricated from a material selected from the group including but not limited to metal, plastic, composite, and wood. In an example, the jig 315 is fabricated from a material selected from a group including but not limited to polyethylene, polytetrafluoroethylene, stainless steel, and aluminum.

In an embodiment, the dimensions of each portion of the jig 315 are determined with respect to the intended function of the respective component. Notably, the board mount surface 318, the standoff distance 309, and the light mount portion 314 should be sized in order to mount the board, allow for discernible light array projection, and house a properly positioned light source, respectively. In an exemplary embodiment, a height 340 of the jig 315 is determined such that the board mount surface 318 and the light mount portion 314 are relatively dimensioned. In an example, the height 340 of the jig 315 is 45.0 mm. The standoff distance 309, pre-determined in order to provide a discernible reflected light array, is 20.0 mm. In another embodiment, the standoff distance 309 can be modified in order to provide a discernible reflected light array on a board display surface and to ensure clearance of the camshaft lobe from the light source portion 314. The board mount surface 318 of the board mount portion 317 of the jig 315 is dimensioned, via a jig width 341 and a height 345 of the board mount portion 317, in order to couple to the board. In an example, the jig width 341 is 16.0 mm and the height of the board mount portion is 15.0 mm. In an embodiment, a depth 342 of the light mount portion 314 and a depth 343 of the board mount portion 317 are determined such that a board display surface is positioned along a diameter of the light mount clearance 313. In an example, the depth 341 of the light mount portion 314 is 30.0 mm and the depth 343 of the board mount portion 317 is 20.0 mm.

In an embodiment, the tapped hole 316 is sized and threaded according to a pre-determined screw in the context of a selected light source. In an example, the tapped hole 316 is configured to couple with a screw selected from a group including but not limited to an M3 screw. In an embodiment, the light mount clearance 313 is sized in accordance with a diameter of a light source in order to provide free motion of the light source within the light mount clearance 313. In an example, the light mount clearance 313 has a diameter of 10.0 mm.

According to an embodiment, the light source is selected based upon the reflective properties of the light rays from the radial surface of the camshaft lobe. In an exemplary embodiment, the light source is a light source selected from a group including but not limited to an incandescent light bulb, a light-emitting diode, a xenon bulb, a halogen bulb, and a high intensity discharge bulb.

Figure 4:
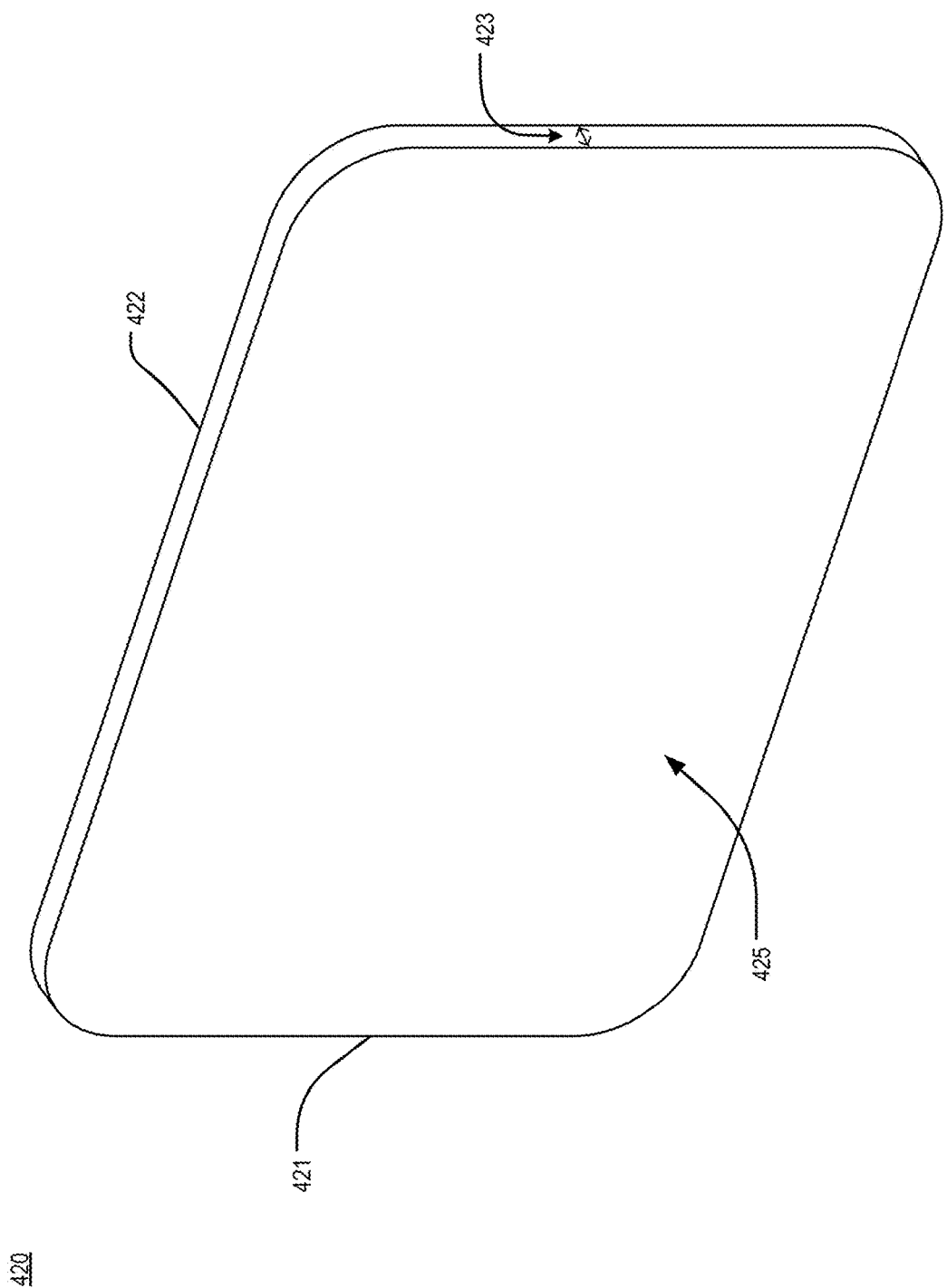
FIG. 4 is a schematic of a perspective view of a board of a chatter evaluation tool, according to an embodiment of the present disclosure.

FIG. 4 is a schematic of a perspective view of a board of the chatter evaluation tool, according to an embodiment of the present disclosure. The board 420 is substantially rectangular with a first board dimension 421, a second board dimension 422, and a third board dimension 423. The first board dimension 421 and the second board dimension 422 form a board display surface 425 on a first surface and a jig mount surface (not shown) on a second surface.

Figure 5:
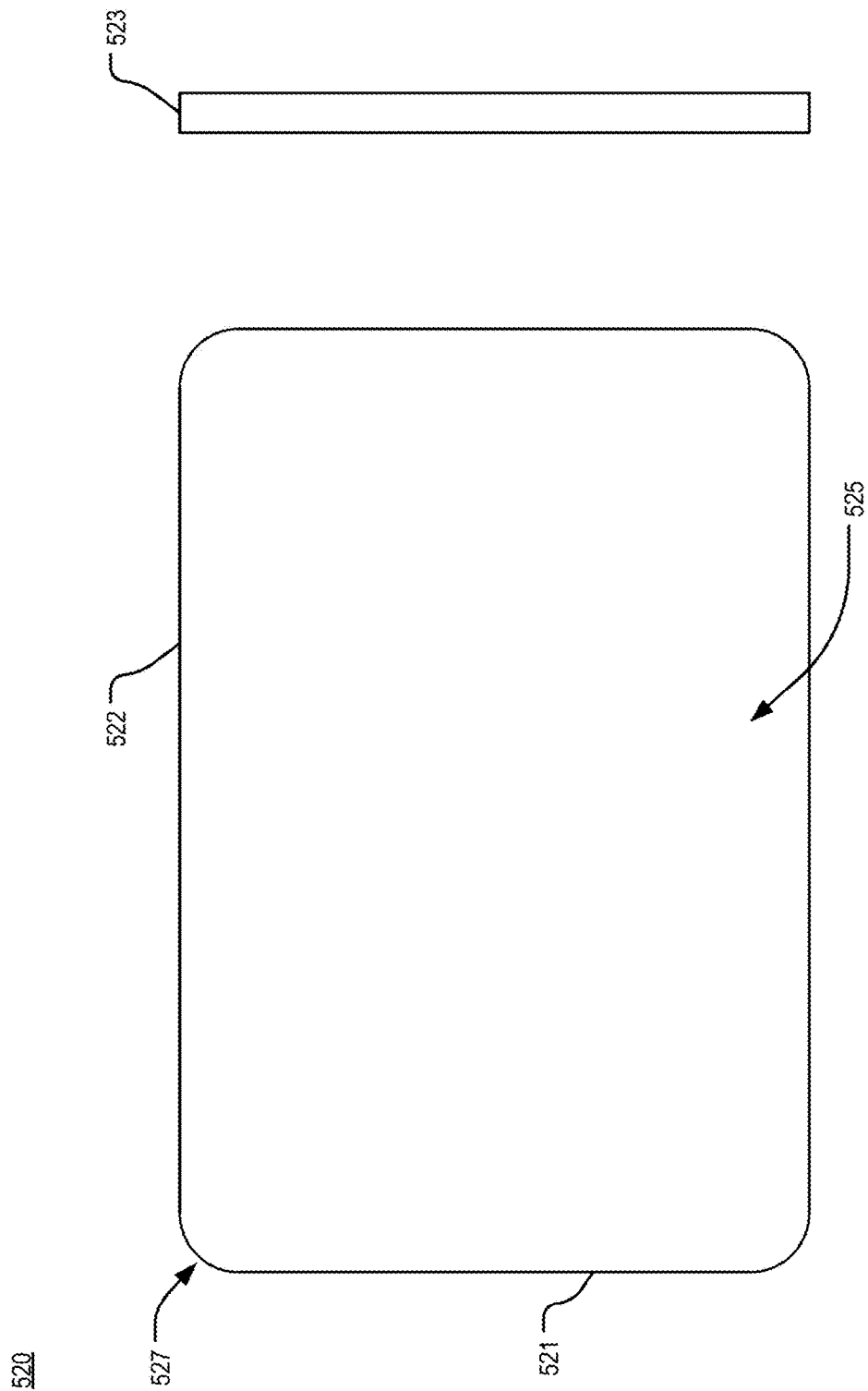
FIG. 5A is a schematic of a frontal view of a board of a chatter evaluation tool, according to an embodiment of the present disclosure.
FIG. 5B is a schematic of a side view of a board of a chatter evaluation tool, according to an embodiment of the present disclosure.

FIG. 5A is a schematic of a frontal view of the board of the chatter evaluation tool, according to an embodiment of the present disclosure. The board 520 comprises a first dimension 521 and a second dimension 522. The first dimension 521 and the second dimension 522 define a board display surface 525 on a first surface and a jig mount surface (not shown) on a second surface. FIG. 5B is a schematic of a side view of the board of the chatter evaluation tool, according to an embodiment of the present disclosure. The board 520 further comprises a third dimension 523.

According to an embodiment, the first dimension 521 and the second dimension 522 are determined in order to provide sufficient display surface for light rays reflected from a radial surface a camshaft lobe and to ensure fixation with a board mount surface of the jig. Therefore, the first dimension 521 of the board 520 is determined according to a first dimension of the camshaft lobe, wherein the first dimension of the camshaft lobe includes but is not limited to a short dimension or a long dimension. In an example, the first dimension 521 of the board 520 is 39.0 mm, corresponding to a long dimension of the camshaft lobe of 25.0 mm. Moreover, the second dimension 522 of the board 520 is determined according to a second dimension of the camshaft lobe, wherein the second dimension of the camshaft lobe includes but is not limited to a short dimension or a long dimension. In an example, the second dimension 522 of the board 520 is 56.0 mm, corresponding to a long dimension of the camshaft lobe of 25.0 mm.

According to an embodiment, the third dimension 523 of the board 520 is determined in order to align the board display surface 525 with a diameter of a light mount clearance of a light mount portion of the jig. In an example, the third dimension 523 of the board 520 is 2.0 mm.

In order to improve user safety, each corner 527 of the board 520 is modified such that a radial edge, or fillet, is created. In an example, each filleted corner 527 has a radius of 5.0 mm.

According to an embodiment, the second dimension 522 of the board 520 and the third dimension 523 of the board 520 form an abutting surface configured to abut a radial surface of a camshaft. In an exemplary embodiment, the abutting surface is a planar surface, as depicted in the schematic of FIG. 5A. In another embodiment, the abutting surface is a concave surface, with a curve along the second dimension 522 of the board 520. In an example, the concave, abutting surface is dimensioned in order to provide a more secure abutment of the board 520 to the radial surface of the camshaft.

According to an embodiment, the board 520 is fabricated from a material such that the first surface may function as the board display surface 525 and the second surface may function as the jig mount surface (not shown). In an exemplary embodiment, the board 520 is fabricated from a material selected from a group including but not limited to metal, plastic, composite, and wood. In an example, the board 520 is fabricated from polyester. In another embodiment, the board 520 is fabricated such that the first surface and the second surface have dissimilar properties. In an example, the first surface is a white, semi-reflective matte surface and the second surface is a black, glossy surface.

Figure 6:
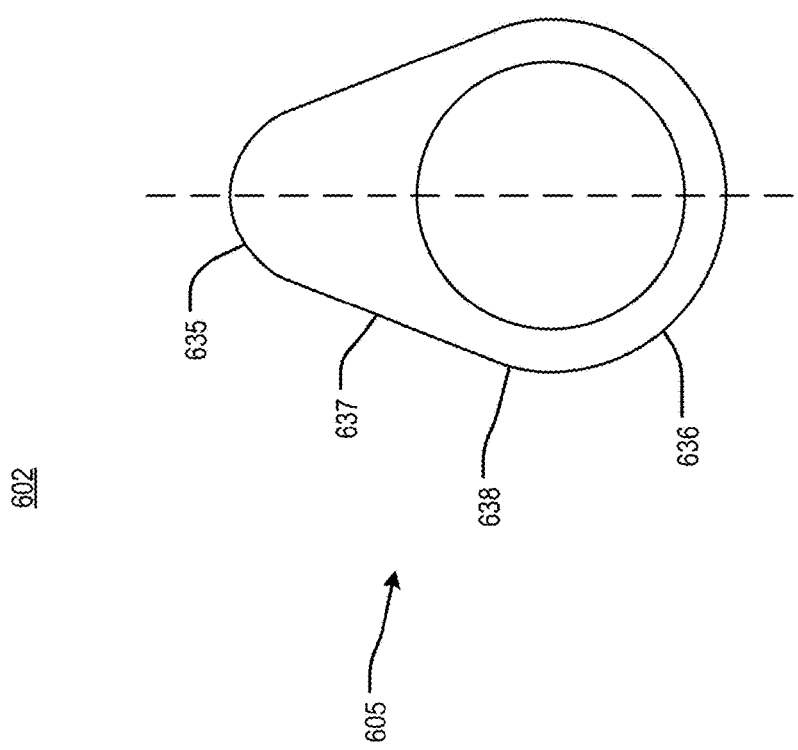
FIG. 6 is a schematic of a camshaft lobe of a camshaft, according to an embodiment of the present disclosure.

Following coupling of the jig with the board, the chatter evaluation tool, with a light source, can be employed along the manufacturing line. Chatter evaluation is performed at several high risk positions along a radial surface of a camshaft lobe. To this end, FIG. 6 is a schematic of a cross section of a camshaft lobe of a camshaft, according to an embodiment of the present disclosure. At one or more surface areas along a radial surface 605 of the camshaft lobe 602, surface roughness evaluations are performed. These one or more surface areas, or high risk positions, include a nose surface 635, a base circle surface 636, and a ramp surface 637. In FIG. 6, these one or more surface areas are described. Further, it is implied that these one or more surface areas are mirrored across the dotted line on the radial surface 605 of the camshaft lobe 602. Each of the one or more surfaces described above are evaluated based upon their role in contacting a piston of an automotive engine, thus creating the possibility of audible chatter. In contrast, a transition region 638 is not evaluated as it is not an area associated with audible chatter.

Figure 7:
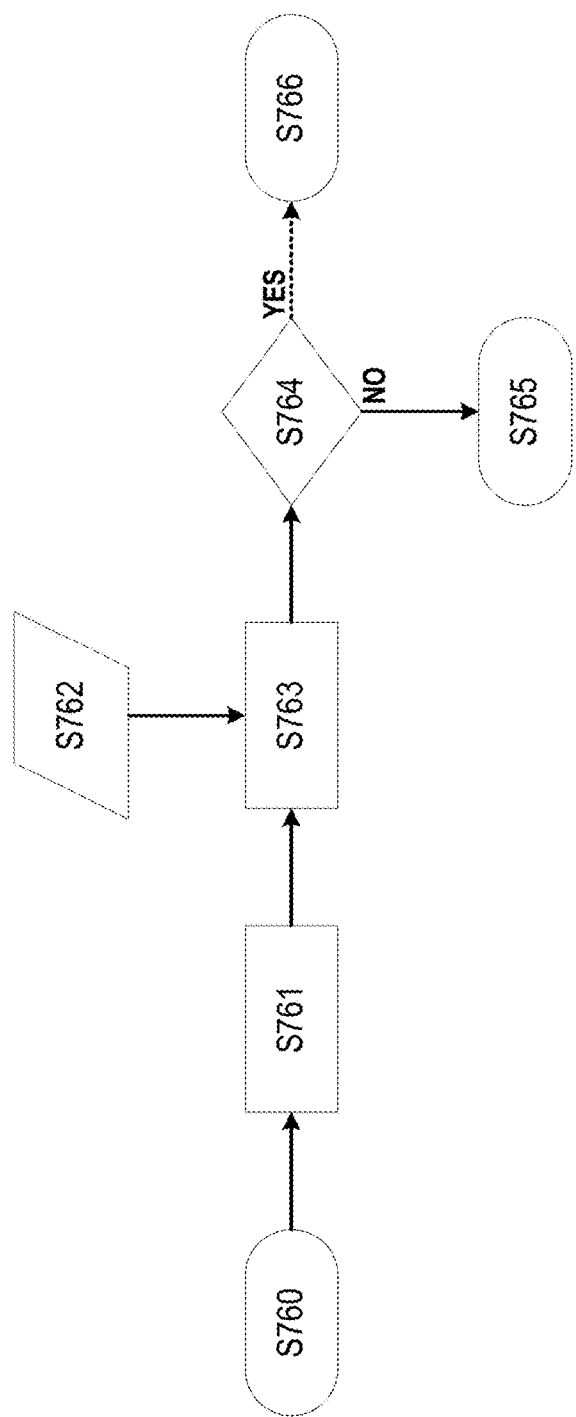
FIG. 7 is a flowchart of a chatter evaluation tool-enabled evaluation sequence of a camshaft lobe, according to an embodiment of the present disclosure.

FIG. 7 is a flowchart of a chatter evaluation tool-enabled evaluation sequence of a camshaft lobe, according to an embodiment of the present disclosure. Initially, a camshaft is transported to a light controlled room and the chatter evaluation tool is positioned on the camshaft proximate to a camshaft lobe S760 such that a board display surface of the board abuts a lateral surface of the camshaft lobe. An emitted light ray axis of the chatter evaluation tool is perpendicular to a long axis of the camshaft. The camshaft is then rotated such that an initial surface area of the camshaft lobe is positioned substantially perpendicular to the light rays of the light source S761. In an embodiment, the initial surface area is a nose surface, base circle surface, or ramp surface of the camshaft lobe. Next, via the reflected light array projected onto the board display surface S762, visually-evaluated chatter is recorded S763. According to an embodiment, chatter is evaluated as a relationship between band thickness, or a width of a ray of reflected light, each ray of reflected light comprising the light array projected onto the board display surface. In an example, narrower bands of reflected light correspond to increased surface roughness and, therefore, increased chatter. Alternatively, thicker bands of reflected light correspond to decreased surface roughness and, therefore, decreased chatter. Following visual evaluation of the chatter of the initial surface area of the camshaft lobe S763, the visually-evaluated chatter is compared with a pre-determined threshold S764 defining an upper limit of acceptable chatter. If it is determined that the visually-evaluated chatter is within the established pre-determined threshold, the camshaft may be further rotated and a subsequent surface area of the radial surface of the camshaft lobe can be evaluated S766, until the camshaft lobe is either approved or it is determined that additional evaluation is required.

In this case, if, the visually-evaluated chatter is outside the established pre-determined threshold, the camshaft lobe must be further evaluated S765 on specialized, highly-automated equipment, and the production line is rendered out of service until the evaluation is complete. While providing accuracy, versatility, and reliability, evaluation via highly-automated equipment is a time-intensive process that may decrease output by unnecessarily requiring production line shutdowns. The ability to rapidly evaluate chatter of the radial surface of the camshaft lobe increases efficiency by decreasing the amount of time expended evaluating a camshaft lobe, thereby minimizing the amount of production line downtime.

Figure 8A:
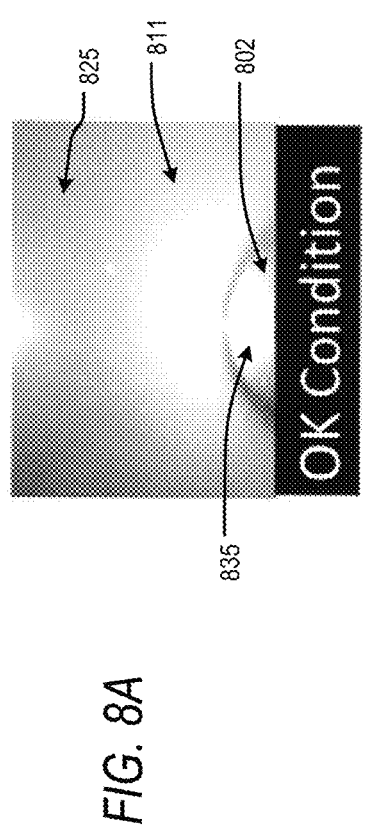
FIG. 8A is an illustration of a reflected light array from a camshaft lobe, according to an embodiment of the present disclosure.
Figure 8B:
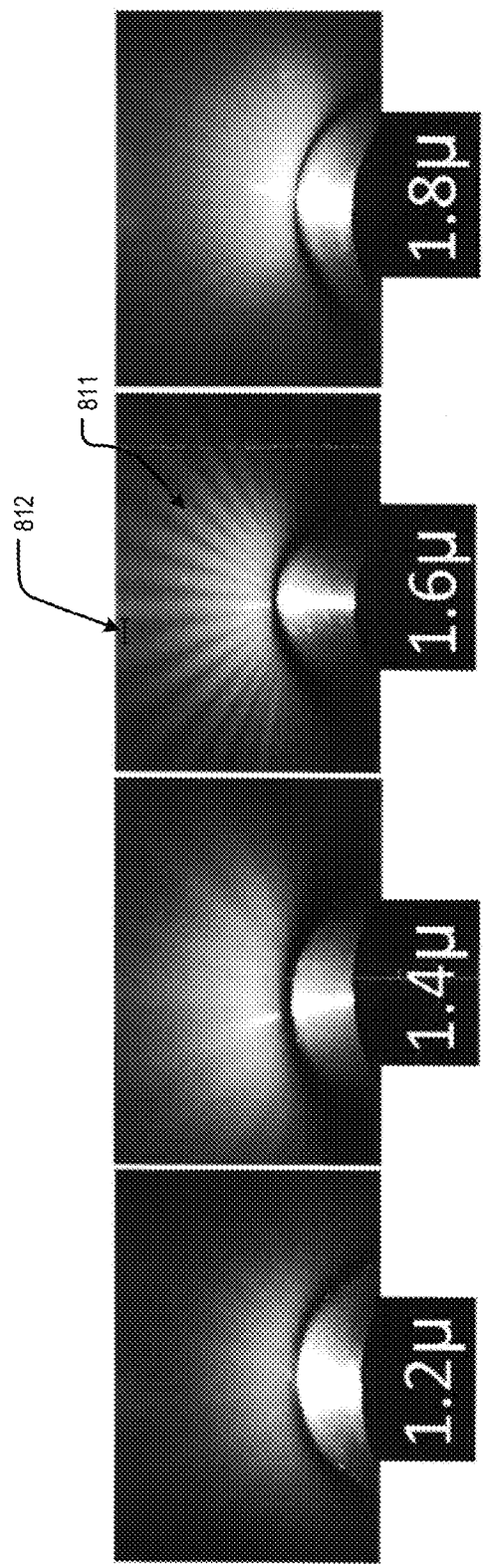
FIG. 8B is an illustration of a variety of reflected light arrays from a camshaft lobe, according to an embodiment of the present disclosure.

FIG. 8A and FIG. 8B are exemplary illustrations of the chatter evaluation tool employed in the evaluation of a camshaft lobe.

FIG. 8A is an illustration of a reflected light array from a camshaft lobe. According to an embodiment of the present disclosure, an emitted light is reflected from a nose surface 835 of the camshaft lobe 802. The reflected light array 811, projected onto the board display surface 825, contains imperceptible light bands indicating a surface with minimal levels of chatter. FIG. 8B is an illustration of a variety of reflected light arrays from the camshaft lobe, when chatter is present. According to an embodiment of the present disclosure, and as earlier described, as band thickness 812 of the reflected light array 811 is decreased, the chatter of the radial surface of the camshaft lobe is increased. In an example, and as seen in FIG. 8B, as band thickness 812 decreases, the visually-evaluated chatter of the nose surface of the radial surface of the camshaft lobe increases from 1.2 μm to 1.8 μm. This chatter metric is indicative of a height difference between a peak and a valley of a defect of the radial surface of the camshaft lobe.

According to an embodiment and as described in FIG. 7, visually-evaluated chatter is compared to a pre-determined threshold to determine if additional surface roughness characterization is appropriate to accurately quantify chatter and assess whether or not additional quality control is necessary. In an exemplary embodiment, the pre-determined threshold at which additional surface roughness characterization is appropriate is based upon a level of audible chatter. In an example, and with reference to FIG. 8B, the pre-determined threshold of visually-evaluated chatter is 1.8 μm.

Figure 9:
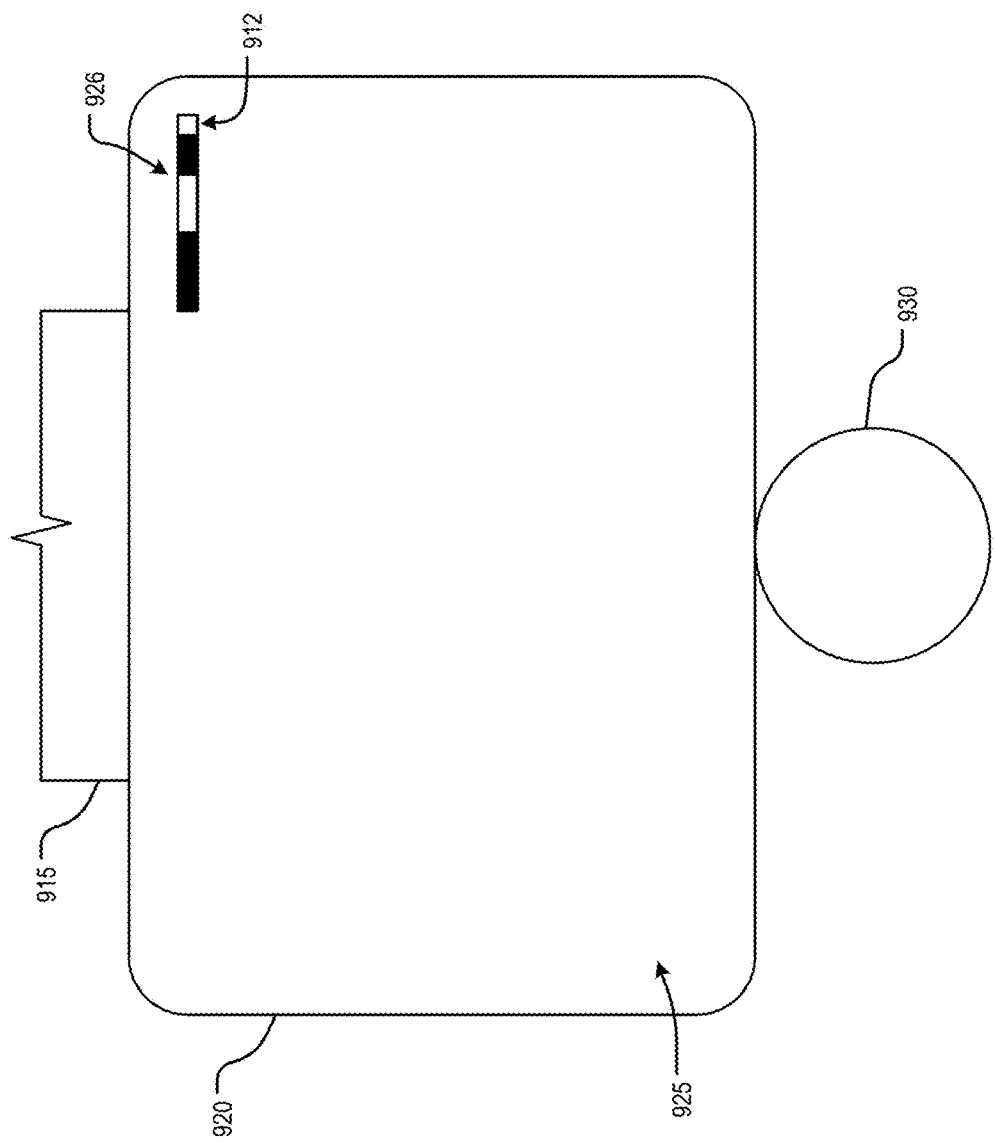
FIG. 9 is a schematic of an aspect of the chatter evaluation tool, according to an exemplary embodiment of the present disclosure.

To aid in visual evaluation of chatter, the chatter evaluation tool may further comprise a grading tool. FIG. 9 is a schematic of an aspect of the chatter evaluation tool. According to an exemplary embodiment of the present disclosure, a board 920 is mounted on a jig 915 and abuts a camshaft 930. A grading aid 926 is disposed on a board display surface 925 of the board 920. The grading aid 926, or scale bar, includes gradations that relate band thickness 912 to chatter level. In an example, in decreasing band thickness 912, the grading aid 926 indicates chatter levels of 1.2 μm, 1.4 μm, 1.6 μm, and 1.8 μm, wherein narrower band thicknesses 912 indicate when additional evaluation is required. According to an embodiment, the above-described grading aid 926 is based upon averaged reference measurements performed via specialized contact or non-contact surface roughness characterization techniques including but not limited to surface profilometry, atomic force microscopy, and scanning electron microscopy.

The chatter evaluation tool, in providing an instant evaluation of surface roughness, aims to improve quality control and manufacturing line efficiency while minimizing production delays.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An apparatus for evaluating a surface roughness of a surface area of a radial surface of a camshaft lobe, comprising:
    a light source having an emitted light ray axis;
    a jig having a light mount portion and a board mount portion; and
    a board having a board display surface and a jig mount surface,
    wherein a standoff distance, defined as a distance between the light mount portion and the board mount portion, is based upon a reflectivity of the surface area of the radial surface of the camshaft lobe, wherein
    the jig mount surface of the board is coupled to a board mount surface of the board mount portion of the jig, and
    the light source is coupled to the light mount portion of the jig.

2. The apparatus of claim 1, wherein the board display surface has a matte surface.

3. The apparatus of claim 1, wherein the emitted light ray axis is parallel to a first dimension of the board.

4. The apparatus of claim 1, wherein the emitted light ray axis forms an angle with a first dimension of the board.

5. The apparatus of claim 1, wherein the emitted light ray axis is perpendicular to a longitudinal axis of a camshaft.

6. The apparatus of claim 1, wherein the board display surface, defined by a first dimension of the board and a second dimension of the board, is perpendicular to a longitudinal axis of a camshaft.

7. The apparatus of claim 1, wherein the light source is disposed along a depth of the light mount portion such that a pre-determined amount of an emitted light is reflected by the surface area of the radial surface of the camshaft lobe.

8. The apparatus of claim 1, wherein the board includes a scale bar disposed on the board display surface, the scale bar describing a relationship between a band thickness and the surface roughness of the surface area of the radial surface of the camshaft lobe, the band thickness being defined as a width of a ray of a reflected light array projected onto the board display surface.

9. The apparatus of claim 8, wherein the scale bar disposed on the board display surface corresponds to a range of surface roughness values between 1.2 μm and 1.8 μm.

10. The apparatus of claim 1, wherein the light source is an incandescent bulb or a light emitting diode.

11. A method for evaluating a surface roughness of a surface area of a radial surface of a camshaft lobe, comprising:
    abutting a board display surface of a board against a lateral surface of the camshaft lobe;
    determining, via a scale bar, a first surface roughness of an initial surface area of the radial surface of the camshaft lobe;
    comparing the first surface roughness of the initial surface area of the radial surface of the camshaft lobe to a pre-determined threshold; and
    determining, via the scale bar, a second surface roughness of a subsequent surface area of the radial surface of the camshaft lobe based upon the comparison of the first surface roughness of the initial surface area of the radial surface of the camshaft lobe and the pre-determined threshold, wherein
    the determining of the surface roughness is based upon a reflected light array projected on the board display surface of the board,
    the board, having the board display surface, is coupled to a board mount surface of a board mount portion of a jig via a jig mount surface,
    the reflected light array is light emitted from a light source coupled to a light mount portion of the jig, the light source having an emitted light ray axis, and
    the light mount portion is separated from the board mount portion by a standoff distance, the standoff distance being based upon a reflectivity of the surface area of the radial surface of the camshaft lobe.

12. The method of claim 11, wherein the board display surface has a matte surface.

13. The method of claim 11, wherein the emitted light ray axis is parallel to a first dimension of the board.

14. The method of claim 11, wherein the emitted light ray axis forms an angle with a first dimension of the board.

15. The method of claim 11, wherein the emitted light ray axis is perpendicular to a longitudinal axis of a camshaft.

16. The method of claim 11, wherein the board display surface, defined by a first dimension of the board and a second dimension of the board, is perpendicular to a longitudinal axis of a camshaft.

17. The method of claim 11, wherein the light source is disposed along a depth of the light mount portion such that a pre-determined amount of an emitted light is reflected by the surface area of the radial surface of the camshaft lobe.

18. The method of claim 11, wherein the scale bar disposed on the board display surface of the board describes a relationship between a band thickness and the surface roughness of the surface area of the radial surface of the camshaft lobe, the band thickness being defined as a width of a ray of the reflected light array.

19. The method of claim 18, wherein the scale bar disposed on the board display surface corresponds to a range of surface roughness values between 1.2 μm and 1.8 μm.

20. The method of claim 11, wherein the light source is an incandescent bulb or a light emitting diode.

\* \* \* \* \*